United States Patent [19]

Austin, Jr.

[11] 4,173,827
[45] Nov. 13, 1979

[54] CONTROL FOR DENTAL HANDPIECES

[76] Inventor: George K. Austin, Jr., P.O. Box 209, Rte. 2, Box 254, Newberg, Oreg. 97132

[21] Appl. No.: 657,146

[22] Filed: Feb. 11, 1976

[51] Int. Cl.[2] .............................................. A61C 19/02
[52] U.S. Cl. ..................................................... 433/98
[58] Field of Search ............................................ 32/22

[56] References Cited
U.S. PATENT DOCUMENTS
3,638,310  1/1972  Austin, Jr. .................................. 32/22

Primary Examiner—Robert Peshock
Attorney, Agent, or Firm—Klarquist, Sparkman, Campbell, Leigh, Hall & Whinston

[57] ABSTRACT

Module control block assemblies are clamped in a bank to individually control to handpieces drive air and air and water coolants and also supply drive air pressure to a gauge through an oversize aligned bore in blocks of the assemblies through which extends a tie rod clamping the assemblies together. The blocks have supply passages therethrough for the above fluids, and covers for the blocks have diaphragm chambers and passages therealong to control flow of the fluids to outlets in the block. Water coolant control valves are mounted on the covers, and are supplied with control air and water coolant from branch passages in the blocks leading to passages through diaphragms and the covers.

11 Claims, 13 Drawing Figures

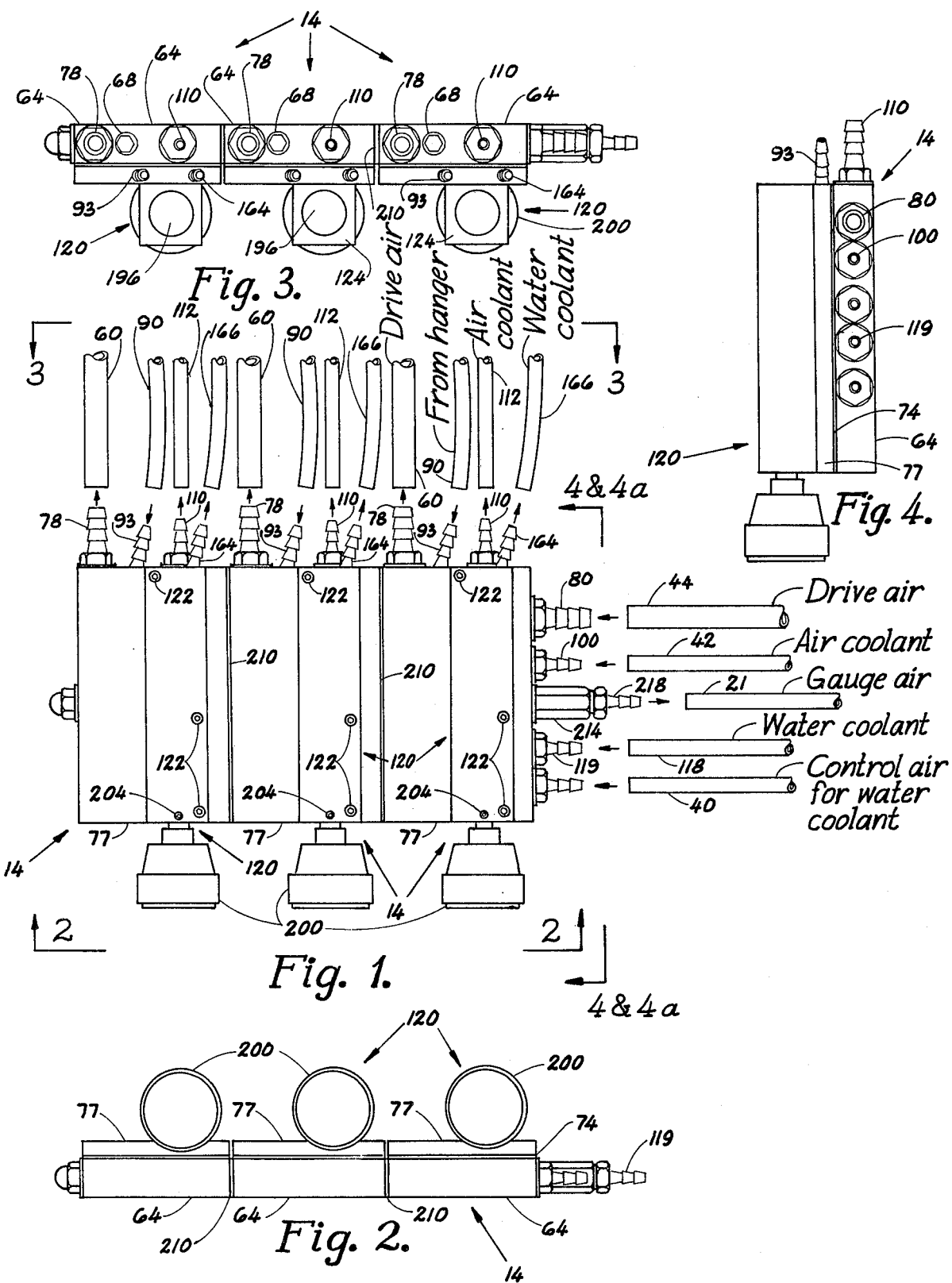

CONTROL FOR DENTAL HANDPIECES

DESCRIPTION

This invention relates to an improved control for dental handpieces, and has for an object thereof the provision of an improved control for dental handpieces.

Another object of the invention is to provide a very compact control for a plurality of dental handpieces.

A further object of the invention is to provide a control for dental handpieces of the module type in which each module includes a water coolant control.

Another object of the invention is to provide a dental handpiece control including a control block assembly having a passaged block and a manifold cover.

Another object of the invention is to provide a dental handpiece control including a control block assembly having a water coolant valve unit.

Another object of the invention is to provide a control for dental handpieces including a plurality of thin blocks secured together in edge-to-edge contact with thin covers having passages and diaphragm chambers secured to the blocks with diaphragm sheets therebetween.

In the drawings:

FIG. 1 is a top plan view of a portion of an improved control for dental handpieces forming one embodiment of the invention;

FIG. 2 is a front elevation view taken along line 2—2 of FIG. 1;

FIG. 3 is an orthographic projection view taken along line 3—3 of FIG. 1;

FIG. 4 is an orthographic projection view taken along line 4—4 of FIG. 1;

Figures 4A, 5, 6:
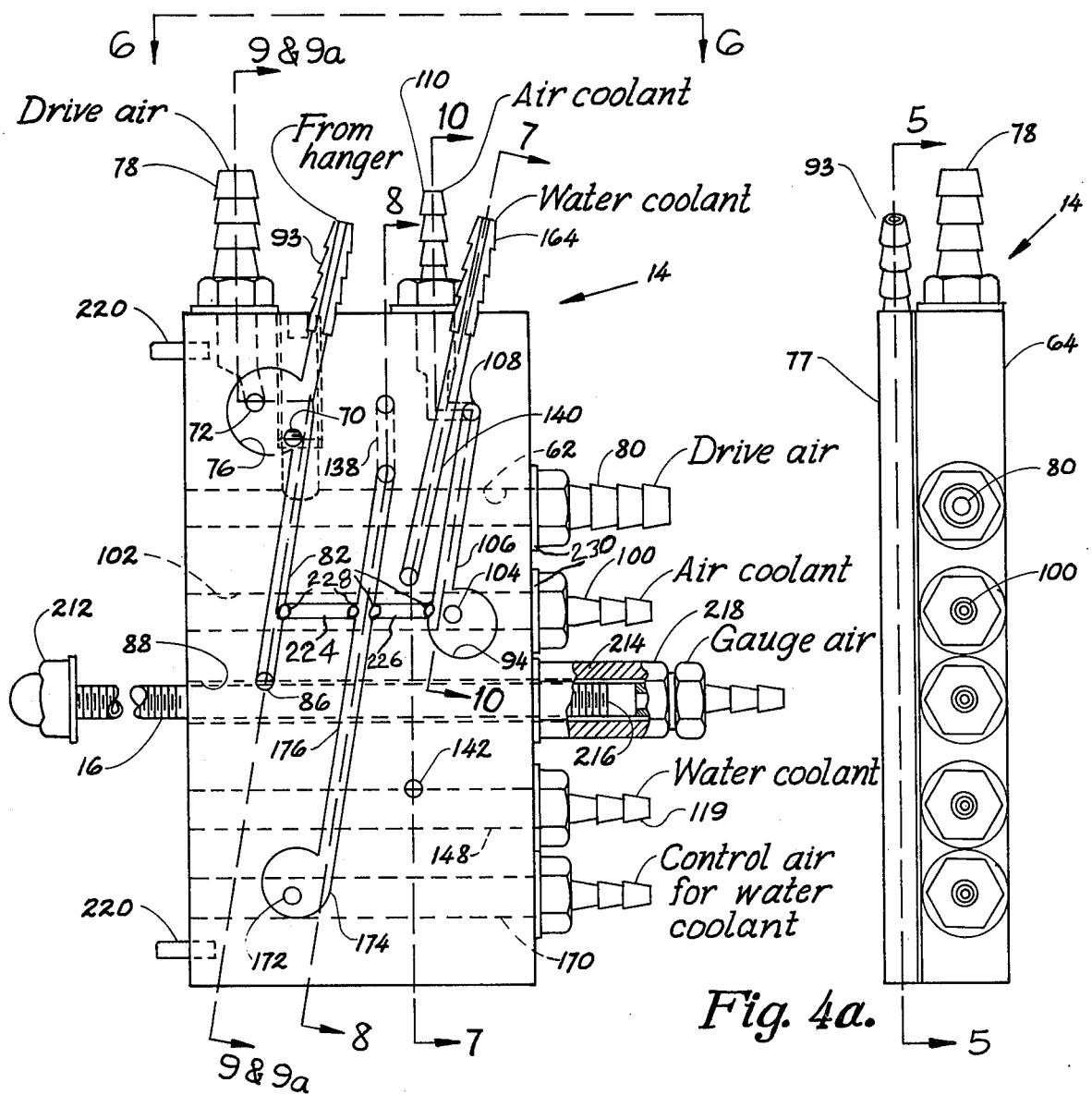
FIG. 5 is an enlarged, top plan view taken along line 5—5 of FIG. 4.
FIG. 6 is an enlarged, front elevation view taken along line 6—6 of FIG. 5.
Figure 11:
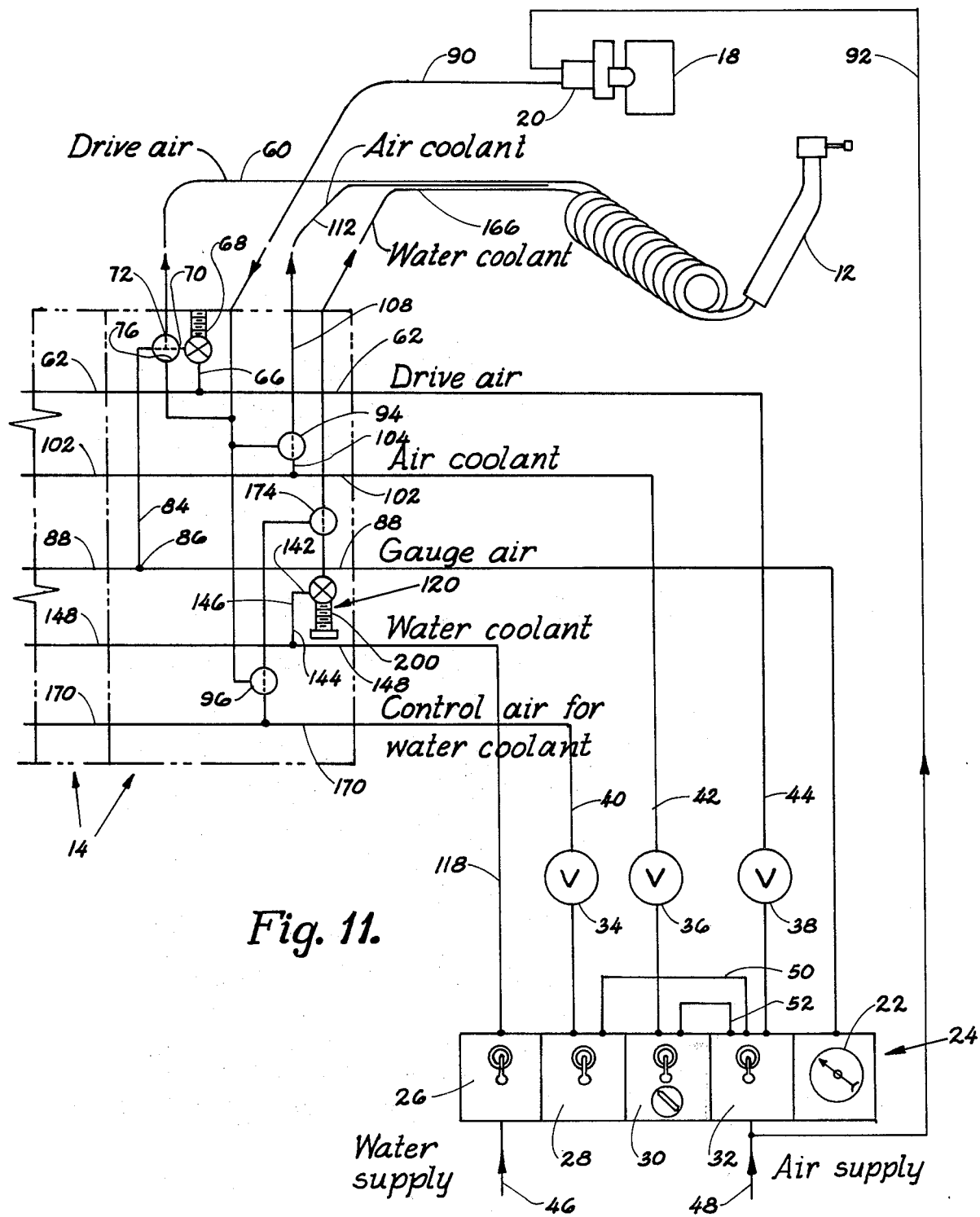

Referring now in detail to the drawings, there is shown therein an improved control for dental handpieces 12 forming one embodiment of the invention and including modular block assemblies 14 clamped in edge-to-edge abutment by a tie rod 16 (FIG. 5), each of the assemblies serving to control supply of drive air, coolant water and coolant air to its handpiece 12 after that handpiece has been lifted from a hanger 18 (FIG. 11) controlling a valve 20 for activating that assembly. Each assembly when activated also connects drive air to a line 21 to an air pressure gauge 22 mounted in a valve block row 24 including a water supply valve 26, control air valve 28, coolant air valve 30 and drive air valve 32. Foot actuated valves 34, 36 and 38 are mounted in lines 40, 42 and 44 from the valves 28, 30 and 32. Coolant water under pressure is supplied to the valve 26 by a line 46, and air under pressure is supplied to the valve 32 by a line 48. Lines 50 and 52 connect this air from the valve 32 to inlets of the valves 28 and 30.

Figure 9:
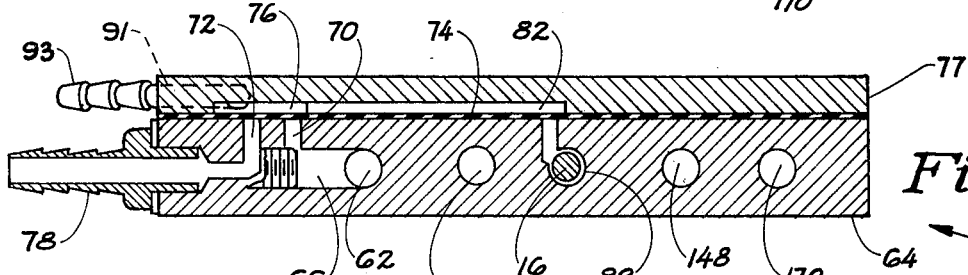
FIG. 9 is an enlarged, vertical sectional view taken along line 9—9 of FIG. 5.
Figure 9A:
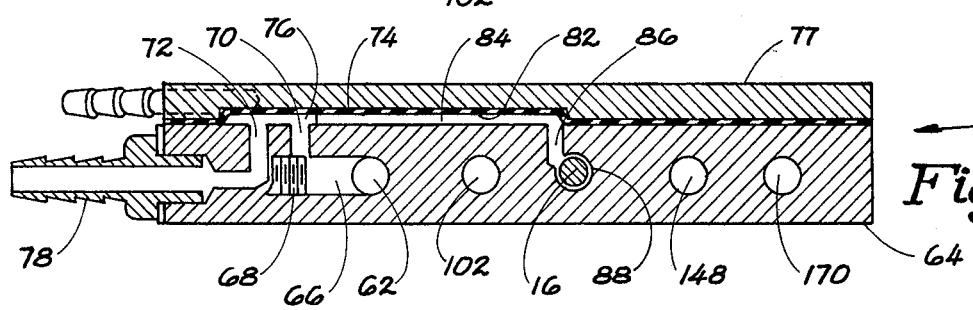
FIG. 9a is a view like FIG. 9 but with parts in different positions.

Drive air from the line 44 is supplied to a line 60 to the handpiece 12 when the handpiece is lifted from its hanger 18 and the valve 38 is pressed by the dentist. The drive air flows from the line 44 to aligned bores 62 in identical, thin blocks 64 (FIG. 2) of the block assemblies 14, from the bore 62 in the block associated with that handpiece through branch bore 66 (FIGS. 9 and 9a), past a screw 68 forming a needle valve, through bores 70 and 72, diaphragm sheet 74 being raised in diaphragm chamber 76 in thin, platelike cover 77 to permit passage from the bore 70 to the bore 72, and through a barb 78 to which the line (hose) 60 (FIG. 11) is connected. A barb 80 (FIG. 5) connects the line (hose) 44 to the bores 62. When air in the diaphragm chamber 76 (FIGS. 9 and 9a) is under pressure, the portion of the diaphragm 74 under the chamber is pressed against planar face of the block 64 to close off the bores 70 and 72 from each other, as shown in FIG. 9. When the pressure of the air in the chamber 76 is reduced to atmospheric pressure, the pressure of the air in the bore 70 pushes the diaphragm 74 up into the chamber 76 as shown in FIG. 9a to open the passage to the bore 72, Also, this air pressure lifts the portion of the diaphragm along a diaphragm groove or runner 82 to open a passage 84 to a branch bore 86 leading to aligned, oversize gauge air bores 88, through which the tie rod 16 extends. When the handpiece 12 (FIG. 11) is in the hanger 18, the valve 20 connects a line 90 connected to a branch line 92 connected to the air supply line 48. The line 90 then supplies air under pressure to diaphragm chambers 76, 82, 94 and 96 to close the valvings of these chambers. When the handpiece is lifted from the hanger, the line 92 is shut off and the line 90 is exhausted to the atmosphere to permit all the valvings under the diaphragm chambers to open. The line 90 is connected to bore 91 (FIGS. 9 and 11) in the cover 77 by a barb 93 screwed into the bore 91.

Figure 7:
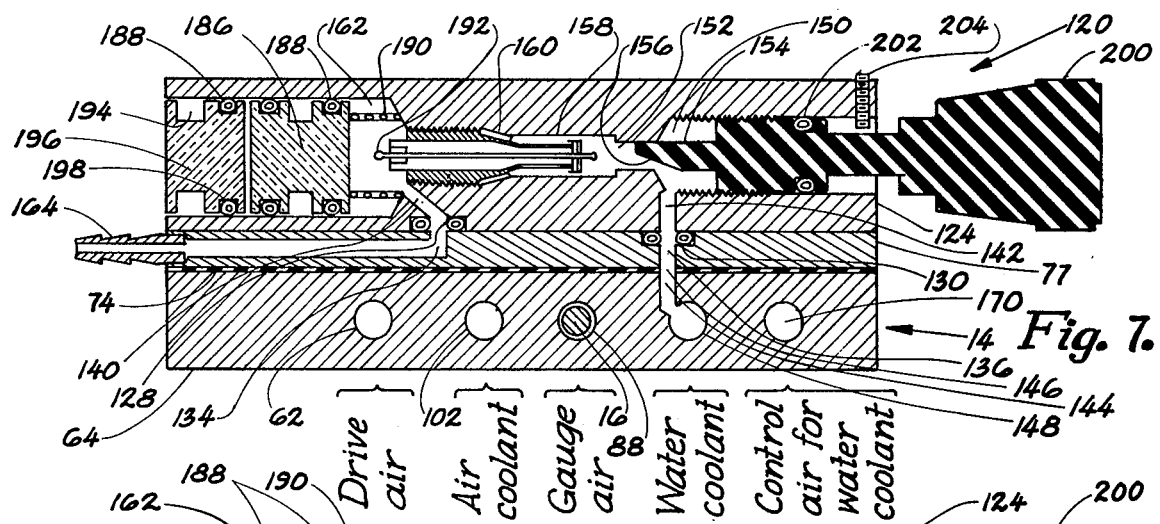
FIG. 7 is an enlarged, vertical sectional view taken along line 7—7 of FIG. 5.
Figure 10:
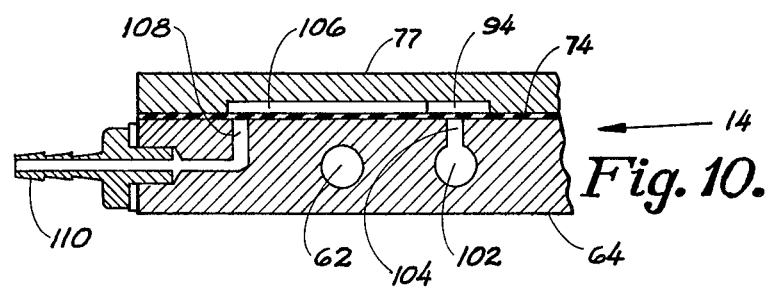
FIG. 10 is an enlarged, fragmentary, vertical sectional view taken along line 10—10 of FIG. 5; and, FIG. 11 is a schematic view of the control of FIG. 1.

Air coolant is supplied to the handpiece 12 (FIG. 11) when the handpiece is lifted from the hanger 18 to exhaust the diaphagm chamber 94 and the foot valve 36 is depressed by the dentist to open it. The air travels from the valves 30 and 36, the line 42 and a barb 100 (FIGS. 7 and 10) into aligned bores 102 in the blocks 64. The air travels from the bore 102 in the block 64 controlling the particular handpiece in use through transverse branch bore 104 (FIGS. 7 and 10) presses the portions of the diaphragm 74 under the circular diaphragm chamber 94 and a diaphragm runner 108 in the cover 77 upwardly into the chamber and runner to form an air passage under the diaphragm, travels along this passage to an L-shaped outlet passage 108, through barb 110 to a line 112 (FIG. 11) to the handpiece. When the handpiece is on its hanger, the portions of the diaphragm 74 (FIG. 10) under the chambers 94 and 96 are pressed down against the planar upper face of the block 64 to close off the bore 104 from the bore 108.

Figure 8:
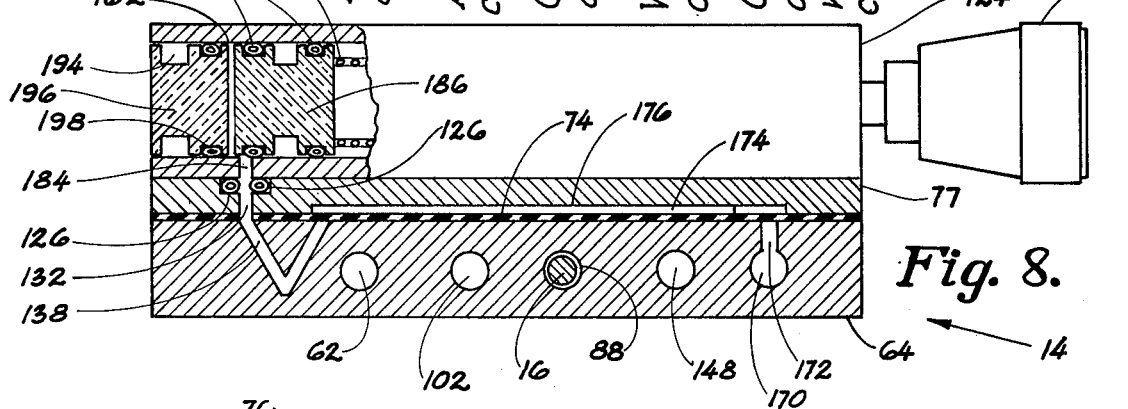
FIG. 8 is an enlarged, vertical sectional view taken along line 8—8 of FIG. 5.

To provide individual adjustment and control of coolant water supplied to the several handpieces from line 46 (FIG. 11) leading from a source of cool water under pressure and valve 26 and line 118 to barb 119 (FIG. 1) each of the control block assemblies 14 includes a valve assembly 120 secured to its associated control block assembly 14 by capscrews 122 screwed into tapped bores in the block 64. These capscrews clamp a block 124 of the valve assembly 120 against the upper planar face of the cover 77 and compressing O-ring gaskets 126, 128 and 130 (FIGS. 7 and 8) partially in annular grooves in the cover and the block 124 to seal passages or bores 132, 134 and 136 in the cover to aligned passages or bores 138, 140 and 142 respectively, in the block 124, the bore 136 being aligned with a branch bore 144 in the block 64 and a hole 146 in the diaphragm sheet 74. The branch bore 146 leads from a coolant water bore 148 in the block 64. The bores 148 in the blocks 64 are supplied with coolant water under pressure by the line 118 (FIG. 11) which connects to the barb 119 (FIG. 1). When the associated handpiece 12 (FIG. 11) is lifted from its hanger 18, the water travels from the bore 148 (FIG. 7) through the bore 144, the hole 146, the bores 136 and 142, a tapped counterbore 150, a cylindrical bore or middle valve passage 152, in which fits a cylindrical needle valving stem 154 having an oblique flat 156, a counterbore 158 into which a tire valve core 160 is screwed, a counterbore 162, the bore 140, the bore 128, the barb 164 and a line 166 to the handpiece.

Water coolant control air is supplied to aligned bores 170 (FIG. 11) in the blocks 64 through the valves 32, 28 and 34 and the line 40. The air travels from the bore 170 of each block assembly 14, when its associated handpiece 12 has been lifted from its hanger 18, through a branch bore 172 (FIG. 8) under the portions of the diaphragm 74 under diaphragm chamber 174 and diaphragm runner 176 (which have been relieved of pressure by lifting the handpiece) to and through the V-shaped bore 138 in the block 64, through the bore 132 in the cover 77, past the O-ring seal 126 in a groove in the cover and through a bore 184 in the valve block 124 and into the counterbore 162 in the block 124 to the left of a piston 186 having O-ring seals 188. The air to the left of the piston pushes the piston to the right against the action of spring 190, and the piston pushes valve stem 192 (FIG. 7) to the right to open the tire valve core 160. The adjacent one of the capscrews 122 extends tangentially through groove 194 in plug 196 carrying O-ring seal 198 to hold the plug in the counterbore 162. The needle valving stem 154 is a portion of an adjusting screw 200 screwed into the tapped counterbore 150 and carrying an O-ring seal 202 and kept from being screwed out of the bore by a blocking screw 204. By screwing the screw 200 farther in, the bore 152 is throttled down further with a needle valve action. When screwed further out, the needle valve passage 152 is opened further.

The blocks 64 (FIG. 2) have gaskets 210 therebetween and the tie rod 16 (FIG. 6) with acorn nut 212 and elongated nut 214 clamp the blocks 64 tightly together. The nut 214 and/or the portion of the rod 16 on which the nut is screwed are longitudinally grooved at 216 to connect the gauge air passage 88 to a barb 218 connected to the hose 21. Dowel pins 220 and holes in the adjacent faces of the blocks 64 align the blocks. Also, in the lefthand one of the blocks 64, as viewed in FIG. 2, plugs (not shown) blocking the lefthand ends of the passages 62, 88, 102, 148 and 170 (FIG. 11) are fixed in the lefthand end portions of those passages in said lefthand one of the blocks. The line 40 is connected to the bore 170 (FIG. 5) by a barb 222. It should be noted that passages 224 and 226 connecting the diaphragm runners 82 and 176 and the diaphragm runner 176 to the diaphragm chamber 94 are bores rather than diaphragm runners, to isolate the passages under the diaphragm chambers 76, 174 and 94 and their associated diaphragm runners 82, 176 and and 106 from each other. Branch ports 228 connect the bores 224 and 226 to the diaphragm runners 82 and 176 and the chamber 94. Gasket washers 230 are provided where necessary.

What is claimed is:

1. In a dental control,
    a thin block having transverse main passages extending from one side edge to the other side edge, branch passages leadng from the main passages to one face of the block, and outlet passages leading from said one face to an end edge of the block,
    a diaphragm sheet on said one face of the block and adapted to close the ends of the branch passages when pressed against said one face of the block,
    and a thin cover on the diaphragm sheet and secured to the block,
    the cover having diaphragm chambers therein opposite the ends of the branch and outlet passages and also having control fluid passages to the diaphragm chambers for pressing the corresponding portions of the diaphragm sheet against said one face of the block,
    some of the diaphragm chambers being circular and some of the diaphragm chambers including long runners extending from one of the circular chambers to another of the circular chambers and adapted to be closed when the corresponding portions of the diaphragm sheet are pressed against said one face of the block.

2. The dental control of claim 1 including a tie rod extending loosely through one of the main passages,
    means for supplying drive air to another of the main passages,
    one of the runners extending from over the branch passage to over the said one of the main passages,
    an air pressure gauge,
    and means connecting said one of the main passages to the air pressure gauge.

3. In a dental control
    a thin block having transverse main passages extending from one side edge to the other side edge, branch passages leading from the main passages to one face of the block, and outlet passages leading from said one face to an end edge of the block,
    a diaphragm sheet on said one face of the block and adapted to close the ends of the branch passages when pressed against said one face of the block,
    a thin cover on the diaphragm sheet and secured to the block,
    the cover having diaphragm chambers therein opposite the ends of the branch and outlet passages and also having control fluid passages to the diaphragm chambers for pressing the corresponding portions of the diaphragm sheet against said one face of the block, and
    valve means mounted on the cover and having an adjustable needle valve therein,
    the block, the diaphragm sheet, the cover and the valve means having a branch passage therethrough from one of the main passages to the needle valve and the valve means having an outlet passage from the needle valve.

4. The dental control of claim 3 wherein the valve means includes a fluid pressure actuated valve in the outlet passage thereof,
    the block having an outlet passage from under one of the diaphragm chambers to a second point on said one face of the block, the diaphragm sheet, the cover and the valve means having a branch passage from said point to the fluid pressure actuated valve to supply actuating fluid to that valve.

5. The dental control of claim 4 including an O-ring surrounding the portion of one of the branch passages at the juncture of the cover and the valve means.

6. The dental control of claim 5 wherein the fluid pressure actuated valve includes an actuator piston and a tire valve core positioned to be actuated by the actuator piston.

7. The dental control of claim 4 wherein the fluid pressure actuated valve includes an actuator piston and a tire valve core actuated by the actuator piston.

8. In a dental control,
a plurality of control block assemblies,
each control block assembly including a control block having an upper face, a pair of opposed side edges, an end edge, main fluid passages extending from one side edge to the other side edge, branch passages extending from the main passage to the upper face, and outlet passages extending from the upper face to the end edge,
a plurality of diaphragm sheets on the upper faces of the control block assemblies for closing the passages opening to the upper face,
a plurality of cover plates on the diaphragm sheets and having diaphragm chambers therein and control fluid passages to the diaphragm chambers,
means securing the blocks in fixed relationship to each other and connecting the main passages of the blocks,
clamping means clamping the blocks in edge-to-edge positions with the main passages in one block aligned with the main passages in the adjacent block,
the clamping means including a tie rod extending loosely through aligned ones of the main passages,
the blocks including outlet passages from the upper faces thereof to the last-mentioned main passages,
and pressure gauge means connected to the last-mentioned main passages.

9. The dental control of claim 8 including a nut and a gasket on one end of the tie rod, a long nut on the other end of the tie rod with a passage formed along the long nut and the tie rod to that end of the tie rod, and a tubular connector screwed into the nut and connecting the interior of the nut to the gauge means.

10. The dental control of claim 9 including a plurality of adjustable needle valve assemblies connected to the covers,
the covers, the diaphragm sheets and the block having passages to the needle valve assemblies.

11. In a dental control,
a plurality of control block assemblies,
each control block assembly including a control block having an upper face, a pair of opposed side edges, an end edge, main fluid passages extending from one side edge to the other side edge, branch passages extending from the main passage to the upper face, and outlet passages extending from the upper face to the end edge,
a plurality of diaphragm sheets on the upper faces of the control block assemblies for closing the passages opening to the upper face,
a plurality of cover plates on the diaphragm sheets and having diaphragm chambers therein and control fluid passages to the diaphragm chambers,
means securing the blocks in fixed relationship to each other and connecting the main passages of the blocks,
and a plurality of needle valve assemblies connected to the covers,
the covers, the diaphragm sheets and the blocks having passages to the needle valve assemblies.

* * * * *